United States Patent [19]
Sullivan et al.

[11] Patent Number: 5,013,308
[45] Date of Patent: May 7, 1991

[54] EXTERNAL MALE CATHETER

[76] Inventors: Mark Sullivan, 26732 Crown Valley Pkwy., No. 111, Mission Viejo, Calif. 92691; Gilbert Salz, 27702 Via Rodrigo, Mission Viejo, Calif. 92692

[21] Appl. No.: 569,431

[22] Filed: Aug. 20, 1990

[51] Int. Cl.⁵ ............................................... A61F 5/44
[52] U.S. Cl. .................................... 604/349; 604/351
[58] Field of Search ...................... 128/760, 842, 844; 604/346, 347, 349, 351, 353; 4/144.1

[56] References Cited

U.S. PATENT DOCUMENTS 4,872,462 10/1989 Salz et al. ............................ 128/842

Primary Examiner—Ronald Frinks
Assistant Examiner—R. Clarke
Attorney, Agent, or Firm—I. Michael Bak-Boychuk

[57] ABSTRACT

An external catheter assembly includes a thin elastomeric membrane attachable to the body of a user and provided with a frustoconical projection feathered in wall thickness towards the opening therein. A first, double-backed adhesive strip is attachable to the membrane around the projection to adhesively engage the open end of an elastomeric sleeve and a second adhesive strip conformed to engage the sleeve, the first strip, and the membrane. The other end of the sleeve extends to a flexible collection container which may include a check valve opposing backflow therefrom.

4 Claims, 2 Drawing Sheets

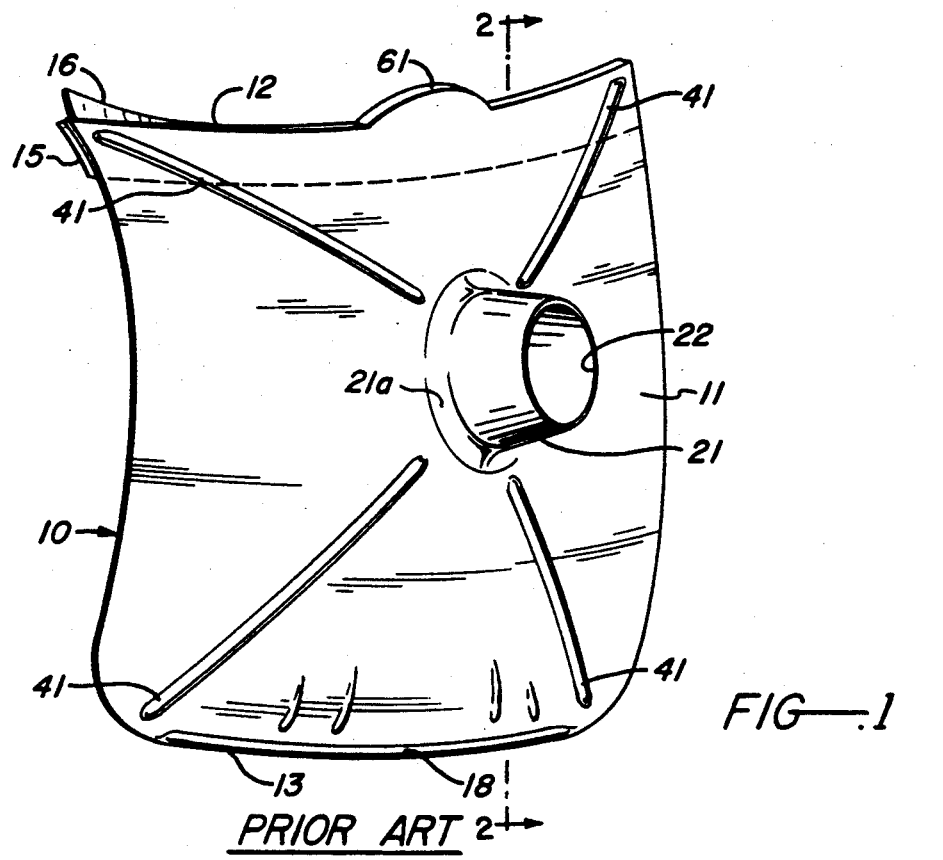
FIG—.1
PRIOR ART
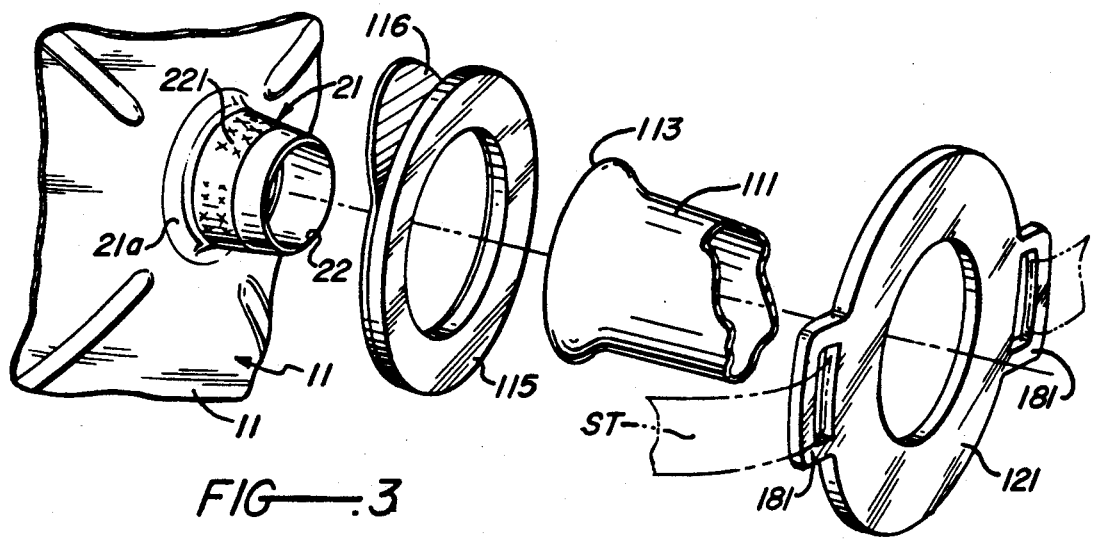
FIG—.3

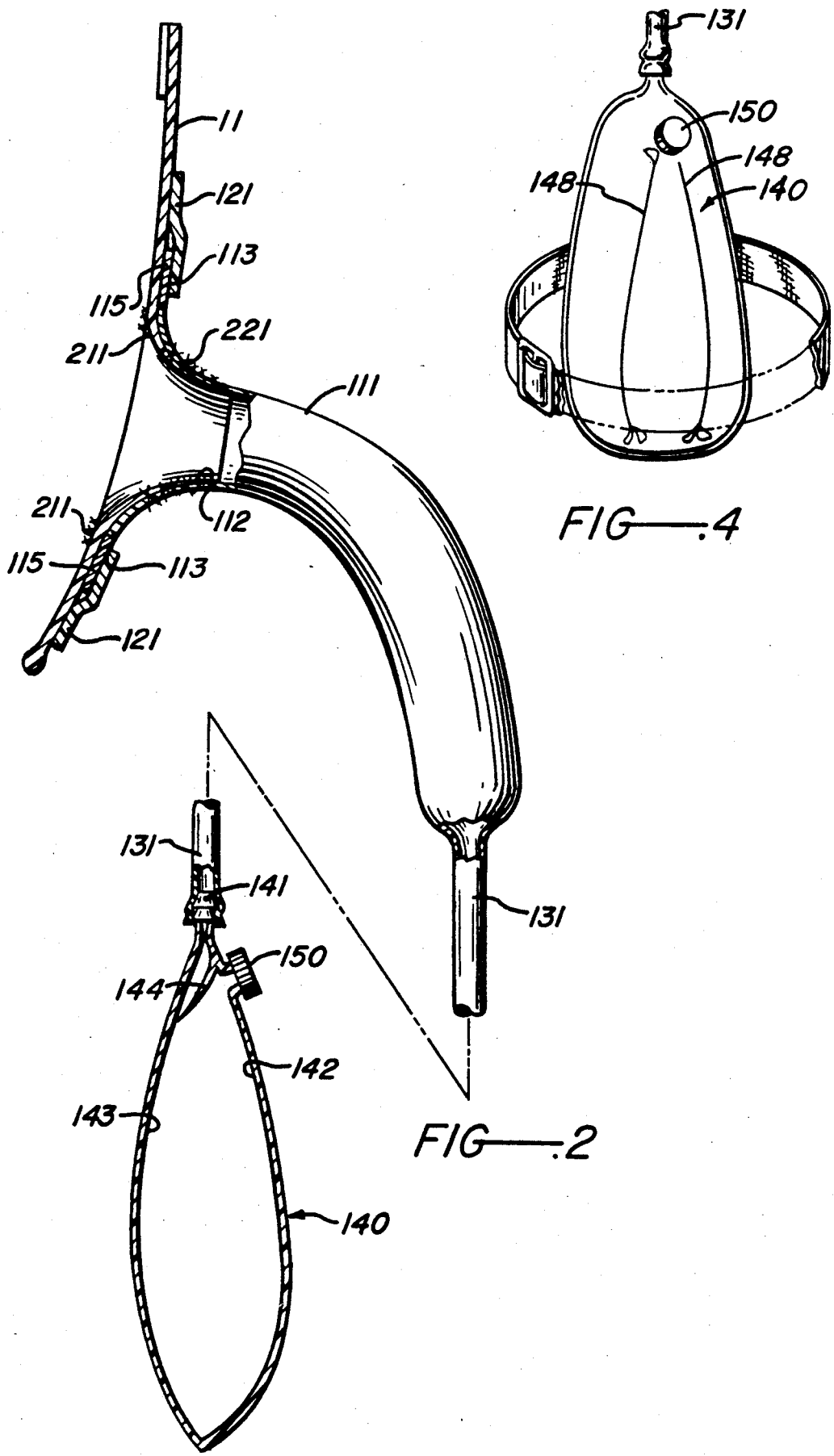

EXTERNAL MALE CATHETER

BACKGROUND OF THE INVENTION

1. Field of the Invention

The present invention relates to external male catheters, and more particularly to external envelopes for containing urine voided by an incontinent patient.

2. Description of the Prior Art

Male urinary incontinence is a matter of substantial discomfort, social embarrassment, and inconvenience. With some frequency the physiological condition leading to urinary incontinence is localized and the patient may be otherwise mobile, functional and capable of ordinary incidents of life. Thus, a conveniently worn external catheter is often desirable, in preference to internal catheters or other containment devices.

External catheters of various forms have been devised in the past, with particular attention to the attachment thereof. Most frequently, such prior art external catheters rely on annular mechanical seals worn at the base of the male organ, pressed against the pubic area. Examples of such sealing mechanisms are found in U.S. Pat. Nos. 3,721,243 to Hesterman et al. and 3,999,550 to Martin. This annular, generally rigid mechanism is then drawn to the body by various straps or other attachments which are often complex, bulky and therefore inconvenient. Thus, while suitable for the purposes intended, these and other prior art devices have had less than full acceptance.

In the past we have devised a flexible shield or barrier useful against transmission of sexually transmitted diseases, which we have described in our U.S. Pat. No. 4,872,462 issued on Oct. 10, 1989. We have since found that the structure disclosed in our prior patent may be useful, in combination with other structures, to effect attachment for an external catheter. It is this structural combination that we now disclose.

SUMMARY OF THE INVENTION

Accordingly, it is the general purpose and object of the present invention to provide an attachment for an external male catheter.

Other objects of the invention are to provide a convenient attachment combination useful with external male catheters.

Yet further objects of the invention are to provide a convenient suspension for external male catheters.

Briefly, these and other objects are accomplished within the present invention by combining the flexible barrier or shield of the type described in our earlier U.S. Pat. No. 4,872,462 with a containment sleeve conformed to receive the male organ. More precisely, the frusto-conical tubular projection of the shield, faired to a thin edge at its end, is coated with a first annular adhesive strip proximate its base. This annular adhesive strip is then useful for engagement of the open end of the containment sleeve. A second annular adhesive strip, of a larger dimension, is then applied over the exterior of the sleeve edge opening, spanning across the contact area of the first strip and extending beyond the sleeve edge to adhere to the shield surface. In this manner a dual adhesive overlap is provided for the containment sleeve while the feather edge of the conical projection effects a seal against the skin.

The containment sleeve is then connected through a conveying tube to a flexible storage bag which may include a check flap against inadvertent back flow.

BRIEF DESCRIPTION OF THE DRAWING

FIG. 1 is a perspective illustration of the prior art shield useful with the present invention;

FIG. 2 is a sectional side view of the inventive external catheter assembly;

FIG. 3 is a perspective illustration, separated by parts, of the sealing engagement useful with the present invention; and FIG. 4 is a perspective illustration of a containment bag useful with the present invention.

DESCRIPTION OF THE PREFERRED EMBODIMENT

The present invention takes benefit of the structural features of a prior art shield described in U.S. Pat. No. 4,872,462 to Gilbert Salz and Mark Sullivan. By reference to FIG. 1 the foregoing prior art shield 10 is briefly summarized as comprising an elastomeric membrane 11 of substantially rectangular planform which, at the upper edge 12, is faced with an adhesive strip 15 covered with a peel-ply layer 16. The lower edge 13 may include an edge bead 18 and radial ribs 41 may be formed in the membrane to control its expanded shape.

At the center membrane 11 includes a frusto-conical projection 21 defined by a faired, substantially larger root circumference 21a and tapering to a smaller opening 22. The surface defining projection 21 is feathered to a thin edge at opening 22 to minimize all constrictive hoop stresses thereat. Further reference for the various structural aspects of the prior art shield 10 should be taken to the teachings of U.S. Pat. No. 4,872,462, which is incorporated herein.

As shown in FIGS. 2-4 the foregoing prior art shield 10 may be useful for a sealing attachment of an external catheter assembly generally designated by the numeral 110. More precisely, assembly 110 includes a generally tubular elastomeric sleeve 111 conformed to receive the male organ and including a faired, expanded, opening 112, once again, of a feathered wall section. The edge 113 of opening 112 may be adhered to an annular, double faced, adhesive strip 115 which is first relieved of its inner peel-ply covering 116 and placed onto membrane 11 in surrounding alignment about the root 21a. The exterior peel-ply 117 is then removed for adhesion of the edge 113. Preferably edge 113 of opening 112 terminates on the exposed adhesive surface leaving a peripheral adhesive portion uncovered. A second peel-plied annual sealing strip 121, of a larger peripheral dimension than strip 115, is then overlaid over the edge 113 to span over the exposed adhesive surface and to bridge onto the membrane 11.

Thus, a redundant sealing arrangement is effected between the opening edge 113 and membrane 11. Internally, sealing contact is effected with the skin surface by the highly compliant feathered edge around opening 22.

The other end of sleeve 111 then reduces to a tubular conduit 131 which may be forced onto a barbed fitting 141 formed on the upper end of a flexible bag 140. An inclined elastomeric flap 144 may extend from one interior surface 142 of the bag towards the other interior surace 143, in alignment subjacent the barbed opening. This inclined flap acts as a check valve limiting excessive backflow in the case of changing positions.

To obtain the assistance of gravity bag 140 may be strapped to the leg of the user and may include a capped drain opening 150 aligned towards the adjacent leg surface. Moreover bag 140 may be segmented by bonding seams 148 towards the capped opening to form a labyrinth interior which further limits inadvertent spillage.

One will note that the shield 10 is intended to be discardable. Similarly, sleeve 111, seals 115 and 121, and the associated tubular conduit 131 all comprise inexpensive articles of manufacture and thus may also be discardable. This discardable aspect relieves sanitary concerns and improves convenience.

To further insure the retention of the catheter assembly on the body of the user, and to provide sealing redundancy, the exterior surface of the projection 21 may be covered with an adhesive 221 against which the interior surface of the sleeve 111 may be compressed. Yet another adhesive coating 211 may be circumferentially applied onto membrane 11 around the base of projection 21. The user, then, by shaving the pubic area, provides the further skin contact for the adhesive 211.

In addition, the annular adhesive strip 121 may include retention tabs 181 to which an elastomeric strap ST may be attacked. Strap ST may then be passed around the person of the user in a manner similar to that taught in the prior art.

In this manner full redundancy is obtained both in retention and sealing for comfortable and convenient use.

Obviously many modifications and changes may be made to the foregoing description without departing from the spirit of the invention. It is therefore intended that the scope of the invention be determined solely on the claims appended hereto.

What is claimed is:

1. An external catheter assembly, comprising:
    an elastomeric membrane of substantially rectangular plan form, including a frustoconical projection extending therefrom characterized by a tapered thickness reducing towards an opening therein;
    a first annular adhesive strip attachable to said membrane in surrounding relationship about said projection;
    a cylindrical elastomeric sleeve characterized by an expanded opening at one end thereof, said expanded opening being of a peripheral dimension lesser than the peripheral dimension of said first annular strip, selectively adhered by said expanded opening to said first annular strip;
    a second annular adhesive strip selectively adhered to said sleeve, said first annular strip and said membrane; and
    fluid conveying means connected to the other end of said sleeve.

2. Apparatus according to claim 1 further comprising:
    a flexible container connected to said fluid conveying means.

3. Apparatus according to claim 2 wherein:
    said membrane has means for adhesively engaging a person.

4. Apparatus according to claim 2 wherein:
    said container includes fluid retention means for opposing the return of fluids into said fluid conveying means.

* * * * *